United States Patent [19]

Seiler et al.

[11] Patent Number: 4,556,724
[45] Date of Patent: Dec. 3, 1985

[54] METHOD FOR THE PREPARATION OF MERCAPTO ALKYL SILANES

[75] Inventors: Claus-Dietrich Seiler, Rheinfelden; Hans-Joachim Vahlensieck, Wehr, both of Fed. Rep. of Germany

[73] Assignee: Dynamit Nobel AG, Troisdorf, Fed. Rep. of Germany

[21] Appl. No.: 683,386

[22] Filed: Dec. 19, 1984

[30] Foreign Application Priority Data

Dec. 24, 1983 [DE] Fed. Rep. of Germany ....... 3346910

[51] Int. Cl.$^4$ ............................. C07F 7/08; C07F 7/18
[52] U.S. Cl. .................................................. 556/429
[58] Field of Search ......................................... 556/429

[56] References Cited

U.S. PATENT DOCUMENTS 4,384,132 5/1983 Schwarz et al. .................... 556/427
4,507,490 3/1985 Panster et al. ...................... 556/427

*Primary Examiner*—Paul F. Shaver

*Attorney, Agent, or Firm*—Felfe & Lynch

[57] ABSTRACT

The present invention relates to the preparation of mercapto alkyl silanes. It sets out from the known reaction of halogen alkyl silanes with thiourea and ammonia, in which guanidine hydrohalides are produced. The separation of these guanidine hydrohalides is performed in accordance with the invention by treating the reaction mixture with a chlorinated hydrocarbon at the end of the reaction. The amount of the chlorinated hydrocarbon is between 20 and 100% of the volume of the input halogen alkyl silane. The treatment with the chlorinated hydrocarbon can be performed either by pouring the latter into the still-hot reaction mixture, or by pouring the still-hot reaction mixture into the chlorinated hydrocarbon. It is advantageous for the precipitation solution that forms to have a temperature above 70° C. after the performance of the precipitation. The filtering out of the precipitated guanidine hydrohalide is performed preferably at room temperature.

12 Claims, No Drawings

METHOD FOR THE PREPARATION OF MERCAPTO ALKYL SILANES

BACKGROUND OF THE INVENTION

The subject matter of the invention is a method for the preparation of mercaptoalkylsilanes, in which halogen alkylsilanes are reacted with thiourea and ammonia and then the guanidine hydrochloride that forms is separated.

Of the known methods for the preparation of mercaptoalkylsilanes, one procedure has proven technically feasible, which consists in reacting halogen alkyl silanes with thiourea and ammonia (cf. German Fed. Pat. No. 20 35 619). At the end of the reaction, depending on the halogen alkyl silane used, a two-phase system forms: a lower, heavier phase forms containing mostly the guanidine hydrohalide along with varying amounts of the desired reaction product, and an upper phase containing mostly the mercaptoalkylsilane plus varying amounts of guanidine hydrohalide. The amounts of mercaptoalkylsilane in the lower phase constitute a considerable source of loss; on the other hand, considerable problems arise out of the guanidine hydrohalide content in the mercaptoalkylsilane raw product in the upper phase when it comes to working up the product by distillation. These problems consist, on the one hand, in the fact that the guanidine hydrohalides which distill in the mercaptoalkylsilanes and crystallize in part in the tubes of the columns result in severe impairments of the distillation process. Another disadvantage consists in the fact that turbidity occurs in the mercaptoalkylsilanes produced by the distillation due to the fine precipitation of guanidine hydrohalides, and refuses to go away.

The problem therefore existed of conducting the further processing of the raw product produced in the reaction of halogen alkyl silanes with thiourea and ammonia such that the salt phase is eliminated as a source of loss, that the distillation of the raw mercaptoalkylsilanes takes place unimpaired by crystallizing guanidine hydrohalides, and that the formation of turbidity in the mercaptoalkylsilane distillates is eliminated.

THE INVENTION

As the solution to this problem, a method has been found for the preparation of mercaptoalkylsilanes by the reaction of halogen alkyl silanes with thiourea and ammonia and separation of the guanidine hydrohalide thus formed, which is characterized by the fact that, upon completion of the reaction, the reaction mixture is treated with a chlorinated hydrocarbon and the guanidine hydrohalide thus precipitated is separated in a manner known in itself.

When this procedure is used the disadvantages described above are avoided, and, on the one hand, a precipitate is obtained which is easy to filter out and is free of remanent mercaptoalkylsilanes except for traces, and on the other hand a filtrate that is free of guanidine hydrohalide is obtained. The process can be used in the preparation of mercaptoalkylsilanes of the formula

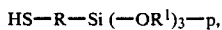

$$HS-R-Si(-OR^1)_{3-p},$$
$$R^2_p$$

wherein R represents an alkylene moiety of 1 to 8 carbon atoms or an alkarylene moiety, $R^1$ represents an alkyl moiety of 1 to 6 carbon atoms, which can be interrupted by oxygen atoms, or an aryl moiety, $R^2$ represents an alkyl moiety of 1 to 8 carbon atoms, or an aryl or alkaryl moiety with preferable 6 to 10 carbon atoms in the aryl moiety and 1 to 8 carbons in the alkyl moiety, and p can assume a value from 0 to 3, which are formed by the reaction of chlorine or bromine compounds corresponding to the above formula with thiourea and ammonia. Preferred compounds to which the method of the invention is applied, are 3-mercaptopropyl-trimethoxysilane, 3-mercaptopropyltriethoxysilane, 3-mercaptopropylmethyldimethoxysilane, 2-mercaptoethyltriethoxysilane, 2-mercaptoethylmethyldiethoxysilane, mercaptomethyltrimethoxysilane, and mercaptopropyldimethylmethoxysilane.

The process, however, is also suitable for the preparation of compounds such as 3-mercaptopropylphenyldimethoxysilane, 3-mercaptopropyltrimethylsilane, mercaptomethylmethyldiethoxysilane, mercaptoethyltrimethoxyethoxysilane, and others.

The chlorinated hydrocarbon is preferably to have a boiling point at or above the temperature which the reaction mixture has at the end of the reaction. The treatment of the reaction mixture with the chlorinated carbon should also be performed as closely as possible to this temperature. Cooling of the reaction mixture to room temperature before adding the chlorinated hydrocarbon is to be avoided.

If cooling occurs before the addition of the chlorinated hydrocarbon, the temperature must not drop to the extent that turbidity or precipitation occurs. In general, this turbidity will not occur in the temperature range between 70 and 120° C. In special situations the temperature can also be lower than this range.

The preferred chlorinated hydrocarbons are those having 1 to 3 carbon atoms; mixtures of these chlorinated hydrocarbons can also be used successfully, and such mixtures can also contain chlorinated hydrocarbons of more than 3 carbon atoms. Both saturated and unsaturated chlorinated hydrocarbons can be used. The preferred chlorinated hydrocarbon is trichloroethylene.

The treatment of the reaction mixture with the chlorinated hydrocarbon can be performed in various ways. It is possible to add the chlorinated hydrocarbon directly to the reaction mixture after the reaction has ended. The addition is performed in such a manner that the mixture does not cool too rapidly, yet frothing of the chlorinated hydrocarbon is avoided. After the addition has been completed the temperature of the mixture is not to have fallen below 70° C. Then a steady cooling to room temperature, i.e., to temperatures below 30° C. is performed, with stirring. Then the separation of the guanidine halide is performed, preferably by filtration.

A variant of the method of the invention is to let the reaction mixture flow into the chlorinated hydrocarbon, with stirring. Here again, the mixture is cooled to room temperature after the addition is completed, and the guanidine hydrohalide is separated at this temperature.

The amount of chlorinated hydrocarbon to be used in the practice of the method of the invention should amount to at least 20% of the volume of the halogen alkyl silane; a volumetric ratio of chlorinated hydrocarbon to halogen alkyl silane of 0.5:1 to 1:1 is preferred. Higher proportions of chlorinated hydrocarbon are not disadvantageous, but they interfere with the subsequent distillation of the products.

Mercaptosilanes are being used increasingly as adhesion promoters between polymers and inorganic solids, and in the modification of silicones.

(A) EXAMPLES FOR COMPARISON PURPOSES

EXAMPLE 1

An enameled 3-cu.m. jacketed reaction vessel equipped with a stirrer, a reflux condenser, a temperature measuring device and gas introduction tubes is filled with 1000 kg of 3-chloropropyltrimethoxysilane and 383 kg of thiourea. The mixture is heated to 110° C. with stirring, and brought to the reaction by the introduction of ammonia at this temperature.

After the reaction has ended, the reaction mixture is cooled to 18° C. within 30 minutes by the introduction of cooling water into the jacket of the reaction vessel. Then it was delivered to a pressure filter (approx. 2 cu.m. capacity; 1.5 m$^2$ filter area) whose filter bottom was equipped with a commercial filter cloth. The mixture to be filtered was put under pressure (1.5 bar) with nitrogen, and the filtration was begun. In just a few minutes the flow of liquid came to a stop, nor could an increase of the pressure in the filter restart the flow of liquid. Then the mixture of salt and liquid was removed from the filter and transferred to a container in which it was allowed to settle. The liquid was siphoned off and delivered to a column for distillation. Then the vacuum distillation was begun to produce the pure mercaptopropyltrimethoxysilane. After just a short time, a strong flocculation of white particles began in the product outlets and in the return line to the top of the column, leading to the clogging of the column control apparatus. The small amounts of product that were found in the distillate receivers were filtered and the filtrates thus obtained were observed for turbidity. The initially clear products turned cloudy after only 2 to 3 days. After another filtration, turbidity was produced again by guanidine hydrochloride precipitating after one week of standing.

A test of the salt residue from the pressure filter shows that what is involved is a slimy mass containing a large amount of mercaptopropyltrimethoxysilane.

EXAMPLE 2

In the apparatus of Example 1, a reaction is performed in the same manner, with the amounts of products specified therein. At the end of the reaction an amount of 500 liters of toluene is added over a period of 25 minutes to the reaction solution whose temperature is 100° C., and the contents of the reactor are then cooled within 30 minutes to 18° C. and delivered to the pressure filter set up as in Example 1. Nitrogen is used to place the product under a pressure of 1.5 bar for filtration. After 50 liters of filtrate are obtained, the filtration process has to be stopped because, despite increasing the filtration pressure, the production of filtrate ceases. When the contents of the filter is dumped, a bulky, slimy precipitate is visible. The same undesirable phenomena occur as in Example 1.

EXAMPLE 3

In the apparatus of Example 1 the reaction is performed with the same amounts of product specified therein, and in the same manner described therein. After the end of the reaction a quantity of 500 liters of octane is added to the 100° C. hot reaction solution, and then the vessel contents are cooled within 30 minutes to 18° C. and delivered for filtration in the pressure filter set up as in Example 1. After establishing a nitrogen pressure of 1.5 bar on the product to be filtered, an amount of about 65 liters of filtrate was obtained in the course of one hour. Then the filtration gradually comes to a stop despite increasing the filtration pressure.

When the filter is dumped, a slimy precipitate becomes visible. Then the same undesirable phenomena occur as in the preceding Examples 1 and 2 given for comparison.

(B) EXAMPLES IN ACCORDANCE WITH THE INVENTION

EXAMPLE 4

In the apparatus of Example 1, a reaction is performed with the amounts and in the manner described therein. At the end of the reaction an amount of 500 liters of trichloroethylene is added to the 100° C. hot reaction solution within 25 minutes; then the reactor content is cooled within 30 minutes to 18° C. and delivered to the pressure filter set up as in Example 1 for filtration. A nitrogen pressure of 1.5 bar is applied and sustained at this level throughout the filtration process.

Within 17 minutes the liquid portion of the precipitation mixture has separated. In the filter remains a dry, granular residue which contains the guanidine hydrochloride in the stoichiometrically expected amount. The mercaptopropyltrimethoxysilane retained in this precipitate amounts to less than 3% of the weight of the amount of silane put in.

The working up of the filtrate by distillation takes place in the manner described in Example 1. Throughout the entire distillation period, no flocculation of guanidine hydrochloride becomes visible in the product drain lines and in the return line to the top of the column. The 3-mercaptopropyltrimethoxysilane captured in the distillate receivers is bottled and tested at monthly intervals for incipient turbidity. In the course of twelve months no alteration was observed in the product.

EXAMPLE 5

In the apparatus of Example 1, a reaction is performed with the amounts and in the manner specified therein. At the end of the reaction an amount of 500 liters of 1,1,1-trichloroethane is delivered into the 90° C. hot reaction solution within 25 minutes. Then the reactor content is cooled within 30 minutes to 18° C. and then drained into the pressure filter set up as in Example 1 for the separation of the precipitate. The filter is put under a nitrogen pressure of 1.5 bar, which is maintained throughout the filtration process. In the course of 19 minutes the liquid content of the precipitation mixture is separated. In the filter remains a dry, granular filter cake which contains the guanidine hydrochloride in the stoichiometrically expected amount. The amount of mercaptopropyltrimethoxysilane retained in this precipitate amounts to less than 3% of the weight of the silane put in.

The working up of the filtrate by distillation takes place in the manner described in Example 1. The results obtained accord with those of Example 4.

EXAMPLE 6

In the apparatus of Example 1, a reaction is performed with the amounts of product and in the manner specified therein. After the end of the reaction, a quantity of 500 liters of carbon tetrachloride is delivered into the 90° C. reaction solution over a period of 25 minutes. Then the reactor content is cooled to 18° C. within 30 minutes and then drained into the pressure filter, set up as in Example 1, for separation of the precipitate. The filter is placed under a nitrogen pressure of 1.5 bar, which is sustained to the end of the filtration. In the course of 21 minutes, the liquid content of the precipitation mixture is separated. In the filter remains a dry, granular residue which contains the guanidine hydrochloride in the stoichiometrically expected amount. The amount of mercaptopropyltrimethoxysilane retained in this precipitate amounts to less than 3% of the weight of the amount of silane put in.

The working up of the filtrate by distillation is performed in the manner set forth in Example 1. The results obtained accord with those of Example 4.

EXAMPLE 7

In the apparatus of Example 1, a reaction is performed with the amounts of product and in the manner specified therein. After the end of the reaction, a quantity of 250 liters of trichloroethylene is fed into the 100° C. solution within 25 minutes. Then the reactor content is cooled within 30 minutes to 18° C. and then drained into the pressure filter set up as in Example 1 for the separation of the precipitate. The filter is placed under a nitrogen pressure of 1.5 bar, which is sustained throughout the filtration process. In 16 minutes the liquid content of the precipitation mixture has separated. In the filter remains a dry, granular residue which contains the guanidine hydrochloride in the stoichiometrically expected amount. The mercaptopropyltrimethoxysilane retained in this precipitate amounts to less than 4.5% of the weight of the silane put in.

The working up of the filtrate by distillation is performed in the manner explained in Example 1. Throughout the entire distillation period no flocculation of guanidine hydrochloride was apparent in the product outlet lines and in the return line to the top of the column. The 3-mercaptopropyltrimethoxysilane that was produced in the distillate receivers is bottled and tested at monthly intervals for incipient turbidity. In the course of twelve months no alteration of the product occurred.

EXAMPLE 8

In an apparatus similar to that of Example 1, 122 weight-parts of 3-bromopropyltrimethoxysilane and 38 weight-parts of thiourea were reacted with ammonia in the manner therein described. After the reaction had ended, 50 parts by volume of trichloroethylene were added to the 100° C. solution within 25 minutes, and then the precipitation mixture was cooled to 18° C. within 30 minutes. For the separation of the precipitate, the contents of the reactor were drained into the pressure filter set up as in Example 1 and a nitrogen pressure of 1.5 bar was applied and sustained throughout the filtration period. In the course of 21 minutes the liquid content of the precipitation mixture is separated. In the filter remains a dry, granular residue which contains the guanidine hydrobromide in the stoichiometrically expected amount. The content of mercaptopropyltrimethoxysilane retained in this precipitate amounts to less than 3.5% of the weight of the silane put in.

The working up of the filtrate by distillation is performed in the manner set forth in Example 1. No flocculation of guanidine hydrobromide becomes visible in the product output lines and in the return line to the top of the column at any time during the distillation. The 3-mercaptopropyltrimethoxysilane which collected in the distillate receivers is bottled and examined at monthly intervals for incipient turbidity. No alteration of the product is observed in the course of 12 months.

EXAMPLE 9

In an apparatus corresponding to Example 1, and in the manner described therein, 84 weight-parts of 3-chloropropyldimethylmethoxysilane and 38 weight-parts of thiourea are reacted with ammonia. At the end of the reaction, 50 parts of trichloroethylene by volume are added to the solution, still at 100° C., over a period of 25 minutes. Then the precipitation mixture obtained is cooled within 30 minutes to 18° C. and drained into the pressure filter set up as in Example 1 for separation of the precipitate. Throughout the filtration period a pressure of 1.5 bar is applied to the filter. In the course of 16 minutes the liquid content of the precipitation mixture is separated. In the filter remains a dry, granular residue containing the guanidine hydrochloride in the stoichiometrically expected amount. The content of mercaptopropyldimethylmethoxysilane retained in this precipitate amounts to less than 4% of the weight of the input silane.

The working up of the filtrate by distillation takes place in the manner described in Example 1. Throughout the entire distillation period, no flocculation of guanidine hydrochloride is observed in the product output lines or in the return line to the top of the column. The distillates manifest no alteration over an observation period of 12 months.

EXAMPLE 10

In an apparatus similar to Example 1, 99 weight-parts of 2-chloroethylmethyldiethoxysilane and 38.3 weight-parts of thiourea are reacted with ammonia in the manner described therein. After the end of the reaction 50 volume-parts of 1,1,1-trichloroethane are added within 25 minutes to the solution whose temperature is 90° C. Then the precipitation mixture obtained is cooled within 30 minutes to 18° C. and drained into a pressure filter set up as in Example 1. A pressure of 1.5 bar is applied to the filter throughout the filtration period. In the course of 20 minutes the liquid content of the precipitation mixture is separated. In the filter remains a dry, granular residue which contains the guanidine hydrochloride in the stoichiometrically expected amount. The amount of 2-mercaptoethylmethyldiethoxysilane retained in this precipitate amounts to less than 3.5 percent of the weight of the input silane.

The distillation of the filtrate is performed in the manner described in Example 1. No flocculation of guanidine hydrochloride is visible throughout the entire distillation period in the product outlet lines and in the return line to the top of the column. The distillates manifest no alteration over an observation period of twelve months.

EXAMPLE 11

In an apparatus corresponding to Example 1, in the manner described therein, 86 weight-parts of chloromethyltrimethoxysilane and 38 weight-parts of thiourea are reacted with ammonia. At the end of the reaction a quantity of 50 volume-parts of 1,1,1-trichloroethane is added over a period of 25 minutes to the precipitation mixture obtained. Then the precipitation mixture is cooled to 18° C. within 30 minutes and drained into a pressure filter set up as in Example 1. A pressure of 1.5 bar is applied to the filter throughout the filtration period. In the course of 21 minutes the liquid content of the precipitation mixture is separated. On the filter remains a dry, granular residue which contains the guanidine hydrochloride in the stoichiometrically expected amount. The amount of mercaptomethyltrimethoxysilane retained in this precipitate is less than 4.5% of the weight of the input silane.

The working up of the filtrate takes place in the manner described in Example 1. No flocculation of guanidine hydrochloride becomes visible in the product outlet lines or in the return line to the top of the column at any time in the entire distillation period. The distillates manifest no alteration during an observation time of twelve months.

EXAMPLE 12

In the apparatus of Example 1, and in the manner described therein, a test is performed in which 1000 kg of 3-chloropropyltrimethoxysilane and 383 kg of thiourea are reacted with ammonia. At the end of the reaction the reaction product, at a temperature of 110° C., is made to flow within 25 minutes, with stirring, into a 3-cu.m. jacketed vat which is equipped with a stirrer and reflux condenser and in which 500 liters of trichloroethylene have previously been placed, the temperature dropping to 75° C. Then the vat contents are cooled to 18° C. within 30 minutes and the precipitate is filtered out within 60 minutes in the pressure filter set up as in Example 1, under a nitrogen pressure of 1.5 bar. On the filter remains a dry, granular salt which contains the guanidine hydrochloride in the stoichiometrically anticipated amount. The mercaptopropyltrimethoxysilane retained in this precipitate amounts to less than 3% of the weight of the input silane.

The distillation of the filtrate takes place as described in Example 1. No flocculation of guanidine hydrochloride is seen in the product outlet lines and in the return line to the top of the column throughout the filtration period. The distillates manifest no alteration over an observation period of twelve months.

It will be understood that the specification and examples are illustrative but not limitative of the present invention and that other embodiments within the spirit and scope of the invention will suggest themselves to those skilled in the art.

What is claimed is:

1. In a method for the preparation of mercaptoalkylsilanes by the reaction of halogen alkyl silanes with thiourea and ammonia and separation of the resulting guanidine hydrohalide, the improvement comprising the steps of, after the reaction of halogen alkyl silanes with thiourea and ammonia and before separating the guanidine hydrohalide, treating the reaction mixture with a chlorinated hydrocarbon.

2. The method of claim 1, wherein the chlorinated hydrocarbon is added to the reaction mixture after the end of the reaction.

3. The method of claim 1 wherein the reaction mixture, after the end of the reaction, is poured into a chlorinated hydrocarbon.

4. The method of claim 1 wherein between 20 and 100 volume-percent of the chlorinated hydrocarbon is used, with respect to the initial amount of halogen alkyl silane.

5. The method of claim 4 wherein a chlorinated hydrocarbon or mixture of chlorinated hydrocarbons containing 1 to 3 carbon atoms, is used.

6. The method of claim 5 wherein the treatment with the chlorinated hydrocarbon is performed in the temperature range between 70° and 120° C.

7. The method of claim 6 wherein a temperature of 90° C. to 110° C. is used.

8. The method of claim 1 wherein the separation of guanidine halide comprises filtering off the guanidine halide at a temperature between 0° to 30° C.

9. The method of claim 1 wherein a chlorinated hydrocarbon, or mixture of chlorinated hydrocarbons having 1 to 3 carbon atoms, is used.

10. The method of claim 9 wherein the chlorinated hydrocarbon is trichloroethylene.

11. The method of claim 10 wherein the treatment with the chlorinated hydrocarbon is performed in the temperature range between 70° and 120° C.

12. The method of claim 11 wherein a temperature of 90 ° C. to 110° C. is used.

* * * * *